United States Patent
Fischer et al.

(10) Patent No.: US 7,626,168 B2
(45) Date of Patent: Dec. 1, 2009

(54) METHOD FOR REDUCING CONDENSATION WATER IN GAS SENSOR ARRANGEMENTS

(75) Inventors: Joerg Fischer, Munich (DE); Marco Forlenza, Neuried (DE); Robert Frodl, Munich (DE); Rudi Minuth, Freising (DE); Kuno Straub, Freising (DE); Thomas Tille, Munich (DE)

(73) Assignees: Tyco Electronics Raychem GmbH, Ottobrunn (DE); Bayerische Motoren Werke Aktiengesellschaft, Munich (DE)

( * ) Notice: Subject to any disclaimer, the term of this patent is extended or adjusted under 35 U.S.C. 154(b) by 823 days.

(21) Appl. No.: 11/166,593

(22) Filed: Jun. 24, 2005

(65) Prior Publication Data

US 2006/0033027 A1 Feb. 16, 2006

(30) Foreign Application Priority Data

Jun. 25, 2004 (DE) .................. 10 2004 030 855

(51) Int. Cl.
*G01N 21/35* (2006.01)
(52) U.S. Cl. ............................................. 250/343
(58) Field of Classification Search ................. 250/343, 250/336.1, 338.1, 341.6, 341.1
See application file for complete search history.

(56) References Cited

U.S. PATENT DOCUMENTS

| | | | |
|---|---|---|---|
| 3,860,344 A | 1/1975 | Garfunkel | |
| 3,935,463 A | 1/1976 | Jacobsen | |
| 5,130,544 A * | 7/1992 | Nilsson | 250/343 |
| 5,163,332 A | 11/1992 | Wong | |
| 5,222,389 A * | 6/1993 | Wong | 73/31.02 |
| 5,340,986 A | 8/1994 | Wong | |
| 5,384,640 A | 1/1995 | Wong | |
| 5,834,777 A * | 11/1998 | Wong | 250/343 |
| 6,353,225 B1 | 3/2002 | Strzoda et al. | |

FOREIGN PATENT DOCUMENTS

| | | |
|---|---|---|
| DE | 199 25 196 C2 | 12/2000 |
| EP | 0 616 207 A2 | 9/1994 |
| WO | WO 00/55603 | 9/2000 |

OTHER PUBLICATIONS

Sensor Technologies, Infrared Gas Detection—The "New" Industry Standard (Jun. 1997 Newsletter) 5 pages.

* cited by examiner

*Primary Examiner*—David Porta
*Assistant Examiner*—Mark R. Gaworecki
(74) *Attorney, Agent, or Firm*—Barley Snyder LLC

(57) ABSTRACT

The present invention relates to a method for measuring the presence and/or the concentration of an analyte by means of a gas sensor arrangement and to a corresponding gas sensor arrangement. The gas sensor arrangement comprises a radiation-emitting radiation source, a gas measuring chamber, which may be filled with a test gas containing at least one analyte to be measured, and at least one radiation-detecting detector device which generates an output signal as a function of the presence and/or the concentration of the analyte. In order to be able to reduce the harmful effects of condensation water, which condenses in the gas measuring chamber, the gas measuring chamber according to the invention is heated before the measurement process, such that the wall of the gas measuring chamber assumes a temperature which lies above the dew point of the test gas.

22 Claims, 2 Drawing Sheets

METHOD FOR REDUCING CONDENSATION WATER IN GAS SENSOR ARRANGEMENTS

FIELD OF THE INVENTION

The present invention relates to a method for measuring the presence and/or the concentration of an analyte by means of a gas sensor arrangement and to an appropriate gas sensor arrangement.

BACKGROUND

Gas sensor arrangements comprising a radiation-emitting radiation source, a gas measuring chamber, which may be filled with a test gas containing at least one analyte to be measured, and at least one radiation-detecting detector device which generates an output signal as a function of the presence and/or the concentration of the analyte are known for the detection of a wide variety of analytes, for example methane or carbon dioxide. Conventional gas sensors, as they are disclosed, for example, in EP 0 616 207 A2, WO 00/55603 A1 or DE 199 251 96 C2, are based on the property of many polyatomic gases of absorbing radiation, in particular in the infrared wavelength region. Said absorption occurs in a wavelength characteristic of the respective gas, for example at 4.24 μm for $CO_2$. By means of infrared gas sensors of this type, it is therefore possible to detect the presence of a gas component and/or the concentration of said gas component in a test gas. Such gas sensors comprise a radiation source, an absorption section, i.e. a measuring chamber, and a radiation detector. The radiation intensity measured by the radiation detector is, according to the known Lambert-Beer law, a measure of the concentration of the absorbent gases. In this respect, as in the case of the so-called NDIR (non-dispersive infrared) sensors, a broadband radiation source may be used and a wavelength of interest may be adjusted via an interference filter or grid. Alternatively, a selective radiation source, for example a light-emitting diode or laser, may be used in conjunction with non-wavelength-selective radiation receivers.

Carbon dioxide detection, in particular, is becoming increasingly important in a large number of fields of application. The quality of the interior air, for example, may thus be monitored, the cleaning cycle of self-cleaning ovens may be monitored, the provision of plants with $CO_2$ in greenhouses may be controlled, in the medical field, for example in anaesthetics, the air breathed by a patient may be monitored and wherever there is a risk of $CO_2$ escaping, for example in correspondingly filled air-conditioning systems, a carbon dioxide sensor may be inserted into a warning system.

In order to increase energy efficiency in heating and air conditioning, carbon dioxide detection may be employed in the automotive industry to monitor the $CO_2$ content of the interior air, so as only to initiate a fresh air supply via appropriate ventilation flap control when required, i.e. in the event of an increased $CO_2$ concentration. Moreover, modern motor vehicle air-conditioning systems are based on $CO_2$ as the coolant, so that, in conjunction with escaping $CO_2$ in the event of possible faults, $CO_2$ gas sensors may also fulfill a monitoring function in the automotive industry. In particular in the automotive industry, sensors of this type must satisfy the highest requirements in robustness, reliability and miniaturizability.

A problem occurring especially in the automotive industry is condensation water in absorption gas sensors. As is generally known, condensation water is always produced when air is cooled on surfaces, of which the temperature is lower than the so-called dew point of the air. The dew point depends on the degree of saturation of the air with water and the air temperature.

When absorption gas sensors are used for detecting, for example, $CO_2$ in the interior air of a motor vehicle the problem occurs that, when the internal surface of the wall of the gas measuring chamber exhibits a temperature that is equal to or less than the dew point of the test gas, condensation water condenses on the inner surface of the gas measuring chamber. Said condensation water significantly impairs the measurement process and may also cause damage to the gas sensor arrangement.

An object of the present invention is accordingly to provide a method for measuring by means of a gas sensor arrangement as well as a generic gas sensor arrangement, in which the harmful effects of condensation water may be reduced.

SUMMARY OF THE INVENTION

The present invention is based on the idea that condensation from the test gas may be prevented, if the gas measuring chamber is heated before the measurement process, such that the wall of the gas measuring chamber assumes a temperature which lies above the dew point of the test gas. It may thus be ensured that the moisture present in the test gas cannot condense on the inner walls of the gas measuring chamber and an effect of the condensed moisture on the measurement results as well as possible damage to individual components of the gas sensor arrangement, for example by corrosion, may be prevented.

According to an advantageous embodiment of the present invention, the radiation source, which is already present, may be activated to emit radiation before the actual measurement process, such that the thermal dissipation loss is used to heat the gas measuring chamber. This embodiment has the advantage that the device may be particularly easily produced and merely requires a modification to the activation for its production.

A particularly energy-saving and effective form of heating is the pulsed operation of the radiation source.

When using narrow band radiation sources, however, it can happen that the available thermal dissipation loss of the radiation source is not sufficient to heat the inner walls of the gas measuring chamber beyond the respective dew point. In this case, according to a further advantageous embodiment, an additional heating device, for example a heating resistance, optionally also a PTC (positive temperature co-efficient) heating element, may be provided.

In order to ascertain when a measurement process without interfering condensation of moisture from the test gas is possible, the temperature of the wall of the gas measuring chamber may be monitored and compared to the temperature of the test gas, which is also monitored.

Alternatively, or additionally, a timer may be provided, which makes it possible to heat the gas measuring chamber for a specific length of time. Using experimental values, it is possible to determine, for example as a function of a measured external temperature, how long the supply of heat energy is necessary, before an interference-free measurement process may be carried out.

In order, on the one hand, to improve the energy efficiency and accuracy of the actual measurement, and, on the other hand, to make the targeted heating of the inner wall of the gas measuring chamber possible, the wall of the gas measuring chamber may be configured such that it reflects the radiation emitted by the radiation source. This can either be carried out by the use of radiation-reflecting plastics materials or by coating with a metal coating. In an exemplary embodiment, a gold coating may be deposited by sputtering, vapor coating or by means of electroplating.

The advantageous characteristics of the gas sensor arrangement according to the invention can be used, in particular, for the detection of carbon dioxide, for example in the automotive industry, both for monitoring $CO_2$ escaping from leakage points and also for monitoring the air quality in an interior. Naturally, however, the gas sensor arrangement according to the invention can also be used for the detection of any other gases.

BRIEF DESCRIPTION OF THE DRAWINGS

The invention will be described in more detail hereinafter with reference to the advantageous embodiments shown in the accompanying drawings. Similar or corresponding details of the subject according to the invention are provided with the same reference numerals. In the drawings.

DETAILED DESCRIPTION OF THE EMBODIMENT(S)

Figure 1:
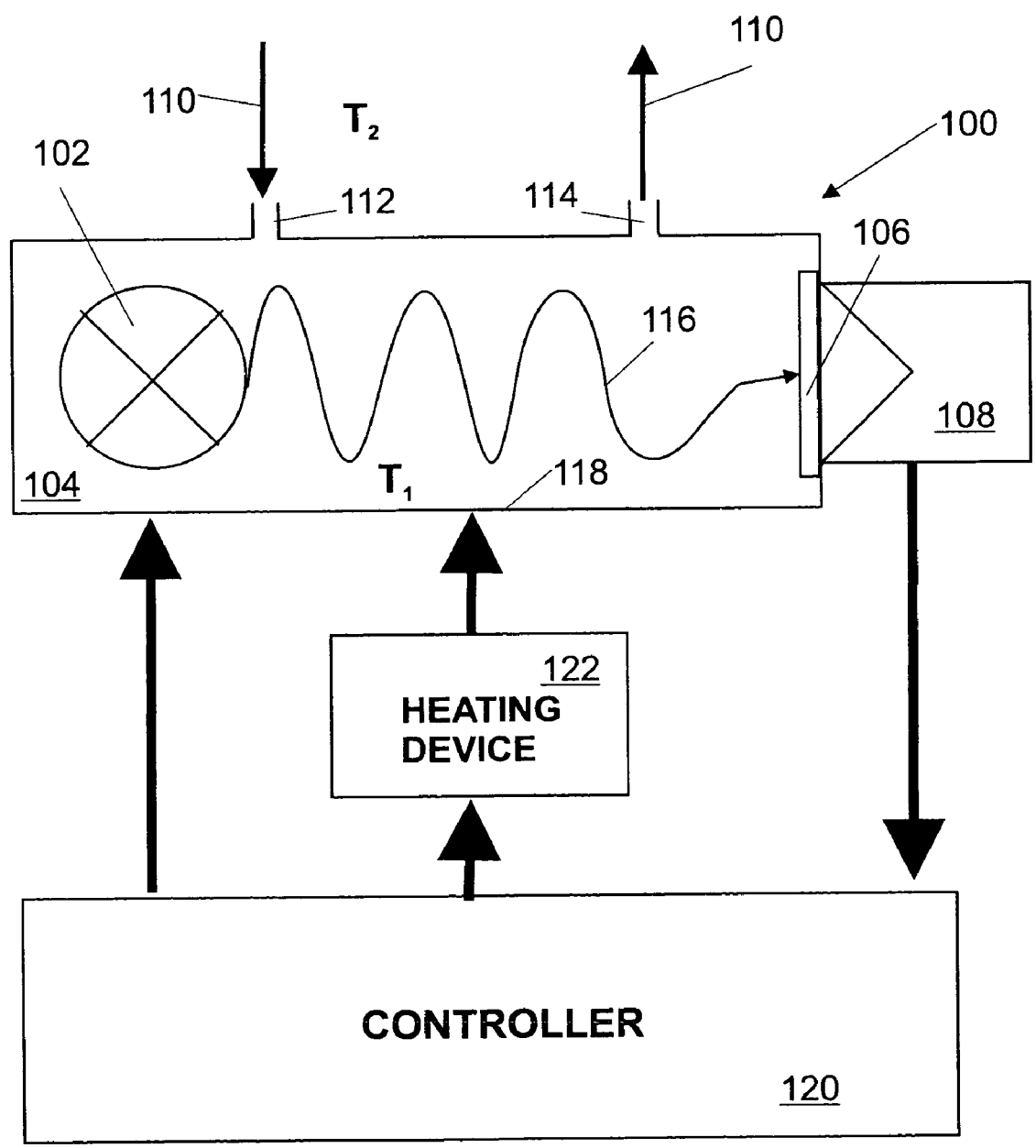
FIG. 1 is a diagrammatic view of a gas sensor arrangement according to a first advantageous embodiment of the present invention.

The construction and the mode of operation of a gas sensor arrangement according to exemplary embodiments of the invention are to be described in more detail hereinafter with reference to the drawing figures.

As shown in FIG. 1, a gas sensor arrangement 100 comprises a radiation source 102, in this case a broadband infrared radiation source. In principle, the gas sensor arrangement 100 shown is a so-called NDIR sensor (non-dispersive infrared sensor). The principal components, in addition to the infrared source 102, which in the simplest of cases is a lamp, are: a gas measuring chamber 104, a wavelength filter 106 and an infrared detector 108.

The test gas 110 is pumped into the gas measuring chamber 104 or diff-used therein, as symbolized by the inlets and outlets 112, 114. The gas concentration can be determined electro-optically via the absorption of a specific wavelength in the infrared range. In this connection the infrared radiation 116 emitted is conveyed to the detector 108 through the gas measuring chamber 104. The detector 108 comprises an optical filter 106, which only allows through the wavelength region, in which the gas molecules to be detected absorb. Other gas molecules generally do not absorb light at this wavelength and do not influence the amount of radiation which reaches the detector. Conventionally, the IR signal from the radiation source is chopped or modulated in order to be able to filter out thermal background signals from the desired signal.

A controller 120 on the one hand activates the radiation source 102 and on the other hand receives the output signals of the detector 108 and processes said output signals further.

In conjunction with the occurrence of condensation water, two temperatures are of vital importance, namely the temperature $T_2$ of the test gas, for example the temperature of the interior air of a motor vehicle, on the one hand and the temperature $T_1$ of the inner wall 118 of the gas measuring chamber 104 on the other hand.

If the temperature $T_1$ of the inner wall of the gas measuring chamber 118 lies below the dew point of the test gas 110, which is determined on the one hand by means of the moisture content of the test gas, but on the other hand also by means of the temperature $T_2$ thereof, condensation water can condense on the inner wall of the gas measuring chamber 118 and sensitively interfere with the test results.

The gas sensor arrangement 100 according to the invention therefore comprises a heating device 122 for heating the gas measuring chamber 104. Said heating device, which is also activated via the controller 120, heats the gas measuring chamber 104 until the temperature $T_1$ of the inner wall 118 of the gas measuring chamber 104 lies sufficiently above the dew point of the test gas 110. Resistance heating, for example, of the type used as a radiation source for heating laser diodes (see, for example, the German patent application. DE 197 17 145 C2) can be used as a heating device. Alternatively, resistances with positive temperature coefficients, known as PTC elements, may also be used.

The activation of the heating device 122, as will be described in greater detail hereinafter with reference to FIG. 2, can be adjusted by the evaluation of the measured temperature $T_1$ and/or $T_2$ as well as by the use of a timer disposed in the controller.

Figure 2:
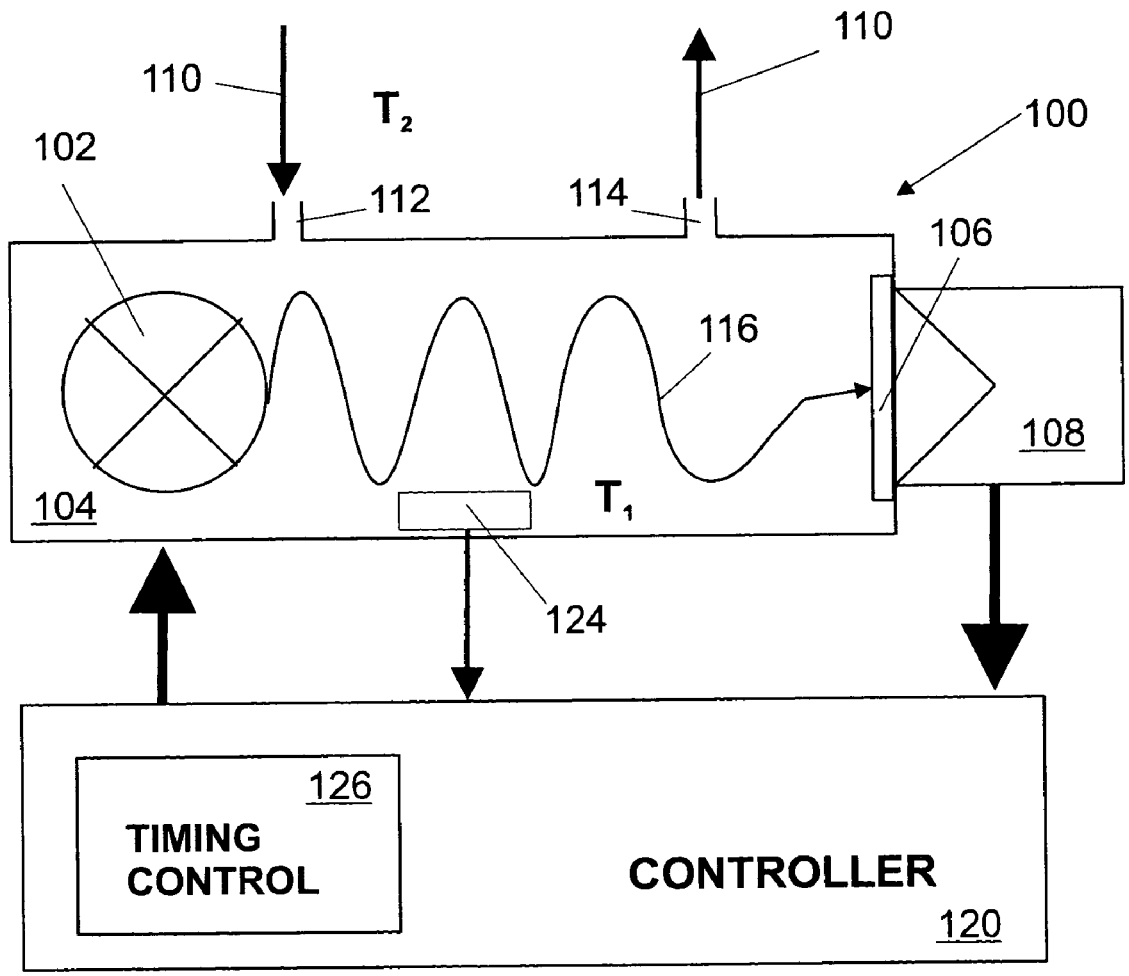
FIG. 2 is a diagrammatic view of a gas sensor arrangement according to a second advantageous embodiment of the present invention.

A particular embodiment, which can be produced particularly easily in conjunction with an NDIR sensor, is illustrated in FIG. 2. Here, the radiation source 102 itself is used to heat the gas measuring chamber 104.

According to the invention, in a pulsed mode, for example, the radiation source 102 is switched on for a specific period of time before the actual measurement process is carried out. The thermal dissipation loss of the radiation source is sufficient, in particular when an infrared lamp is used as the radiation source 102 and in the case of mirror plating of the inner wall 118 of the gas measuring chamber 104, to be able to prevent condensation of condensation water. Furthermore, a temperature probe 124, which determines the temperature $T_1$ of the inner wall 118 of the gas measuring chamber and outputs a corresponding signal to the controller 120, may be provided. On the basis of this information and, optionally, the additional information about the temperature $T_2$ of the test gas 110, the controller 120 activates the radiation source 102 in such a way that the inner wall 118 assumes a temperature above the dew point of the test gas 110.

Alternatively, or additionally, the controller 120 may comprise a timer 126, which makes it possible to heat the gas measuring chamber for a specific period. In order, on the one hand, to increase the signal yield, and, on the other hand, to accelerate the heating of the gas measuring chamber via the radiation source 102, the inner wall 118, according to an advantageous embodiment, may be configured so as to reflect infrared radiation.

Although only a single infrared radiation source has been described above, the method according to the invention is also suitable for gas sensor arrangements, which comprise a plurality of radiation sources and/or detectors. In particular, the method according to the invention can also be extended to gas sensor arrangements, in which a measuring radiation source and a reference radiation source are provided.

Furthermore, in the detailed description of the invention mainly air has been mentioned as the test gas and water vapor as the condensing liquid. However, it is clear that the principles of the solution according to the invention may also be adapted to other test gases and other potentially condensing liquids.

What is claim is:

1. A method for measuring the presence or the concentration of an analyte by means of a gas sensor arrangement with at least one radiation-emitting radiation source, a gas measuring chamber, which may be filled with a test gas comprising at least one analyte to be measured, and at least one radiation-detecting detector device, which generates an output signal as a function of the presence or concentration of the analyte, comprising the steps of:
(a) heating of the gas measuring chamber by selectively activating the at least one radiation source, such that a wall of the gas measuring chamber assumes a temperature, which is higher than the dew point of the test gas; and
(b) carrying out the measurement.

2. The method according to claim 1, wherein the heating step comprises:
reflecting at least a portion of the radiation emitted by the at least one radiation source from the wall of the gas measuring chamber, which heats the gas measuring chamber.

3. The method according to claim 1, wherein the radiation source emits radiation pulses for heating the gas measuring chamber.

4. The method according to claim 1, wherein the heating step comprises activation of a heating device for heating the gas measuring chamber.

5. The method according to claim 1, wherein carrying out the measurement process comprises:
emitting infrared radiation by means of an infrared radiation source.

6. The method according to claim 5, wherein the infrared radiation source is a light-emitting diode.

7. The method according to claim 5, wherein the infrared radiation source is a broadband light spectrum-emitting lamp.

8. The method according to claim 1, wherein the heating step also comprises:
monitoring the temperature of the wall of the gas measuring chamber and comparing it with the temperature of the test gas, and
starting the measurement process when the difference between the two temperature values reaches a predetermined desired value.

9. The method according to claim 1 wherein, in the heating step, the gas measuring chamber is heated for a predetermined period.

10. The method according to claim 1, wherein gaseous analytes are detected or the concentration thereof is determined.

11. Gas sensor arrangement comprising at least one radiation-emitting radiation source, a gas measuring chamber, which may be filled with a test gas to be measured for at least one analyte, at least one radiation-detecting detector device, which generates an output signal as a function of the presence or the concentration of the analyte, a controller for activating the radiation source, and a heating device for heating the gas measuring chamber, such that a wall of the gas measuring chamber assumes a temperature, which is higher than the dew point of the test gas, wherein the heating device is formed by the radiation source.

12. The gas sensor arrangement according to claim 11, wherein the controller is configured such that said controller activates the radiation source for emitting radiation, which heats the gas measuring chamber.

13. The gas sensor arrangement according to claim 11, further comprising at least one heating resistance.

14. The gas sensor arrangement according to claim 11, wherein the radiation to be detected is infrared radiation and the at least one radiation source is formed by an infrared radiation source.

15. The gas sensor arrangement according to claim 11, wherein at least one temperature probe is provided in the gas measuring chamber for monitoring the temperature of a wall of the gas measuring chamber.

16. The gas sensor arrangement according to claim 11, wherein the controller comprises a timer for controlling the heating device.

17. The gas sensor arrangement according to claim 11, wherein the wall of the gas measuring chamber is configured in such a way that said wall reflects radiation emitted by the radiation source.

18. The gas sensor arrangement according to claim 17, wherein the wall of the gas measuring chamber is provided with a metal coating.

19. The gas sensor arrangement according to claim 18, wherein the metal coating is a gold coating, deposited via sputtering, vapor deposition or by means of electroplating.

20. The gas sensor arrangement according to claim 11, wherein said gas sensor arrangement is equipped for detecting gaseous analytes, or for determining the concentration thereof.

21. A method for measuring the presence or the concentration of an analyte comprising the steps of:
(a) providing a gas sensor arrangement with at least one radiation-emitting radiation source;
(b) providing a gas measuring chamber, which may be filled with a test gas comprising the analyte to be measured;
(c) providing at least one radiation-detecting detector device, which generates an output signal as a function of the presence or concentration of the analyte;
(d) heating of the gas measuring chamber for a predetermined period, such that a wall of the gas measuring chamber assumes a temperature, which is higher than the dew point of the test gas; and
(e) carrying out the measurement.

22. A gas sensor arrangement comprising at least one radiation-emitting radiation source, a gas measuring chamber, which may be filled with a test gas to be measured for at least one analyte, at least one radiation-detecting detector device, which generates an output signal as a function of the presence or the concentration of the analyte, a controller for activating the radiation source, a heating device for heating the gas measuring chamber, such that a wall of the gas measuring chamber assumes a temperature, which is higher than the dew point of the test gas, and a timer for controlling the heating device.

* * * * *